(12) United States Patent
Ogino et al.

(10) Patent No.: US 7,491,167 B2
(45) Date of Patent: Feb. 17, 2009

(54) IMAGE CAPTURING UNIT FOR ENDOSCOPE

(75) Inventors: Takayuki Ogino, Saitama (JP);
Kazuyuki Yamamoto, Saitama (JP);
Akihiro Ito, Saitama (JP); Seiichiro Okamura, Ibaraki (JP); Tomokazu Yamashita, Ibaraki (JP)

(73) Assignee: Hoya Corporation, Tokyo (JP)

( * ) Notice: Subject to any disclaimer, the term of this patent is extended or adjusted under 35 U.S.C. 154(b) by 314 days.

(21) Appl. No.: 11/427,812

(22) Filed: Jun. 30, 2006

(65) Prior Publication Data

US 2007/0004964 A1  Jan. 4, 2007

(30) Foreign Application Priority Data

Jul. 1, 2005  (JP) ............................ 2005-193226

(51) Int. Cl.
*A61B 1/04* (2006.01)
*H04N 5/225* (2006.01)

(52) U.S. Cl. ........................... 600/109; 348/65; 348/340

(58) Field of Classification Search ................. 600/109, 600/110; 348/65, 76, 272, 294, 340
See application file for complete search history.

(56) References Cited

U.S. PATENT DOCUMENTS

| | | | |
|---|---|---|---|
| 6,564,018 B2 * | 5/2003 | Melman et al. ............. | 396/429 |
| 6,933,962 B2 | 8/2005 | Yamamoto | |
| 7,022,066 B2 * | 4/2006 | Yokoi et al. ................. | 600/109 |
| 2004/0189854 A1 * | 9/2004 | Tsukamoto et al. ......... | 348/340 |
| 2005/0163016 A1 * | 7/2005 | Kimura .................. | 369/112.01 |
| 2005/0275741 A1 * | 12/2005 | Watanabe et al. ........... | 348/340 |
| 2006/0152615 A1 * | 7/2006 | Kwon et al. ................. | 348/340 |

FOREIGN PATENT DOCUMENTS

| | | | |
|---|---|---|---|
| JP | 62281465 A | * | 12/1987 |
| JP | 10-074865 | | 3/1998 |
| JP | 2003-100920 | | 4/2003 |

OTHER PUBLICATIONS

U.S. Appl. No. 11/427,821 to Ogino et al., filed Jun. 30, 2006.
U.S. Appl. No. 11/456,253 to Ogino et al., filed Jul. 10, 2006.
U.S. Appl. No. 11/456,281 to Yamamoto et al., filed Jul. 10, 2006.
U.S. Appl. No. 11/456,288 to Yamamoto et al., filed Jul. 10, 2006.
English language Abstract of JP 2003-100920.
English language Abstract of JP 10-074865.

* cited by examiner

*Primary Examiner*—John P Leubecker
(74) *Attorney, Agent, or Firm*—Greenblum & Bernstein, P.L.C.

(57) ABSTRACT

An image capturing unit for an electronic endoscope, includes an image capturing element with an image capturing area, at least one bonding wire, which is extended curvedly and outwardly from at least one edge portion of a surface of the image capturing element to at least one conductor, and a transparent cover plate, which is fixed to a frame and is adapted to seal the image capturing element from an external environment. The cover plate is formed to have at least one bonding wire preventing portion, which is adapted to prevent the at least one bonding wire from being in contact with the cover plate. An edge portion on a front surface of the cover plate is hermetically sealed to the frame.

3 Claims, 6 Drawing Sheets

IMAGE CAPTURING UNIT FOR ENDOSCOPE

BACKGROUND OF THE INVENTION

The present invention relates to an image capturing unit that is adapted to be built in a tip portion of an electronic endoscope.

Generally, an image capturing unit of an electronic endoscope including a solid-state image capturing element is provided with bonding wires that conduct electricity to a conductive material arranged behind the solid-state image capturing element. The bonding wires are loosely bent in a front space of the solid-state image capturing element and arranged to extend from edges of an image capturing area outwardly. Such an image capturing unit is generally further provided with a transparent cover glass to protect the solid-state image capturing element, which is fixed to a frame of the image capturing unit. Examples of such an image capturing unit are disclosed in Japanese Patent Provisional Publication Nos. 2003-100920 and HEI 10-74865.

As an inserted portion of a tip of the endoscope is adapted to be inserted into live bodies, the image capturing unit of the endoscope is required to be downsized by tenths of a millimeter to a minimum extent.

In the image capturing units disclosed in the above-referenced publications, however, outlines of the cover glasses are formed to be greater than an area wherein the bonding wires extend, and the cover glasses are arranged to be substantially spaced from the solid-state image capturing element so that the cover glasses do not become in contact with the bonding wires, as the bonding wires may be deteriorated by the contact.

With this structure, downsizing of an image capturing unit for the electronic endoscope is thus limited and it is difficult to configure a diameter of the tip portion to be considerably small. In such a case, a length of a solid portion of the inserted portion tends to be greater, and thus, fine movements of the inserted portion are restricted. As the movements of the inserted portion are restricted, observation capability of the endoscope may be deteriorated. Further, functionalities of an objective optical system of the endoscope, such as a zooming function, may be prevented from being improved.

SUMMARY OF THE INVENTION

In view of the foregoing drawbacks, the present invention is advantageous in that an image capturing unit for an electronic endoscope, in which a cover glass, to be arranged in a tip portion thereof, can be configured to be smaller. With the image capturing unit, the tip portion of the endoscope can be downsized while functionalities of the endoscope may be improved.

According to an aspect of the present invention, there is provided an image capturing unit for an electronic endoscope, including a solid-state image capturing element with an image capturing area, which is adapted to capture an image of an object, at least one bonding wire, which is extended curvedly and outwardly from at least one edge portion of a surface of the solid-state image capturing element to at least one conductor, the at least one conductor conducting electricity to the solid-state image capturing element via the at least one bonding wire, and a transparent cover plate, which is fixed to a frame so that the cover plate is arranged in front of the image capturing element, and is adapted to seal the image capturing element from external environment. The cover plate is formed to have at least one bonding wire preventing portion, which is adapted to prevent the at least one bonding wire from being in contact with the cover plate, so that the at least one bonding wire can be prevented from being interfered by the cover plate when the cover plate is arranged in a position closer to the image capturing element than a position wherein a cover plate without the bonding wire preventing portion is required to be placed. An edge portion on a front surface of the cover glass is airtight or hermetically sealed to the frame.

Optionally, a length between outermost edges of the cover plate may be configured to be greater than a length between the outermost edges of the image capturing area of the image capturing element and to be smaller than a length between a contact point of the at least one bonding wire to the conductor along a first edge of the image capturing element and a contact point of the at least one bonding wire to the conductor along a second edge of the image capturing element.

Optionally, the at least one bonding wire preventing portion may be formed by beveling a rear edge of the cover plate.

DETAILED DESCRIPTION OF THE EMBODIMENTS

Hereinafter, referring to the accompanying drawings, an image capturing unit of an electronic endoscope according to illustrative embodiments of the invention will be described.

First Embodiment

Figure 1:
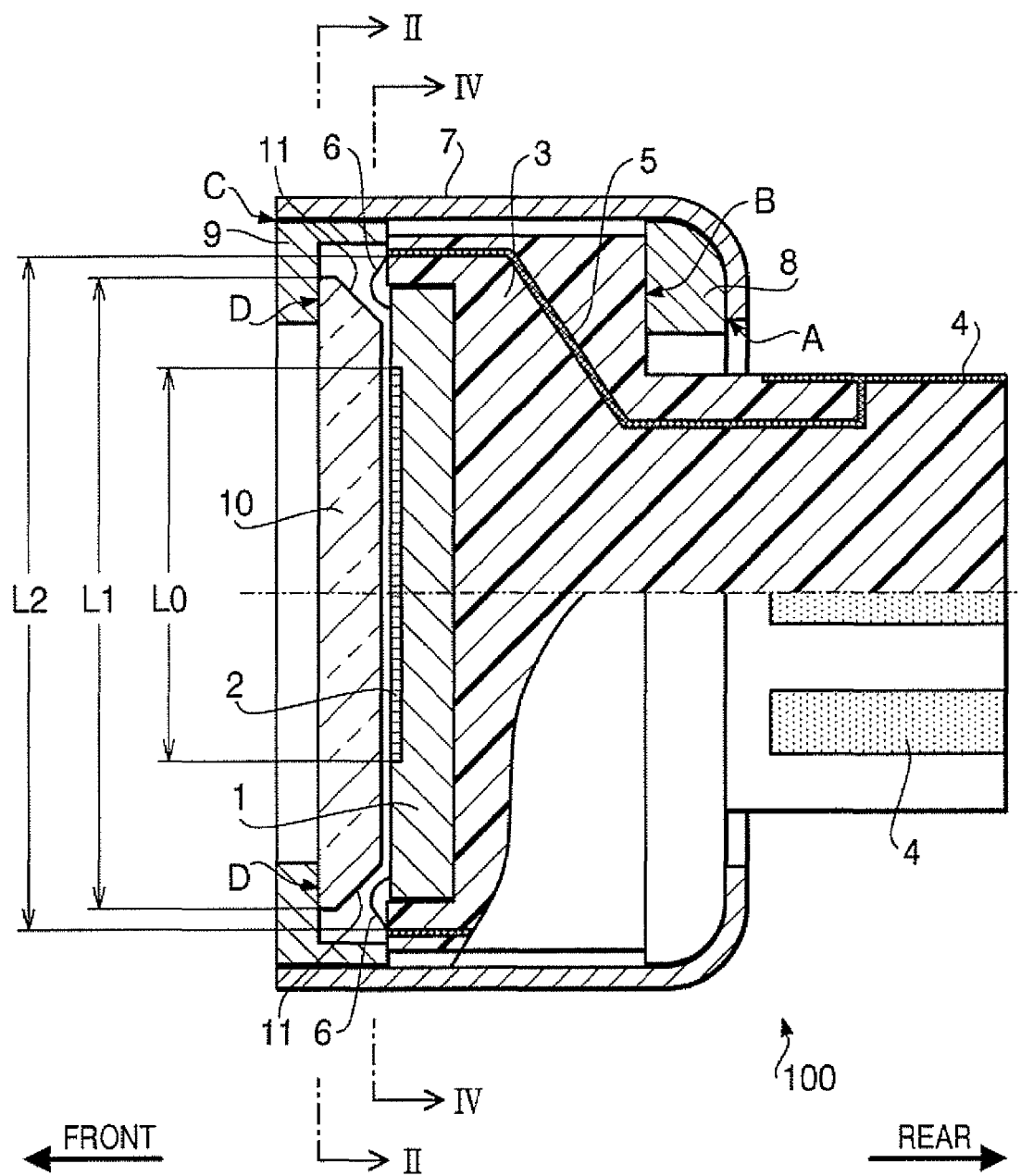
FIG. 1 is a cross-sectional side view of an image capturing unit according to a first embodiment of the present invention.
Figure 2:
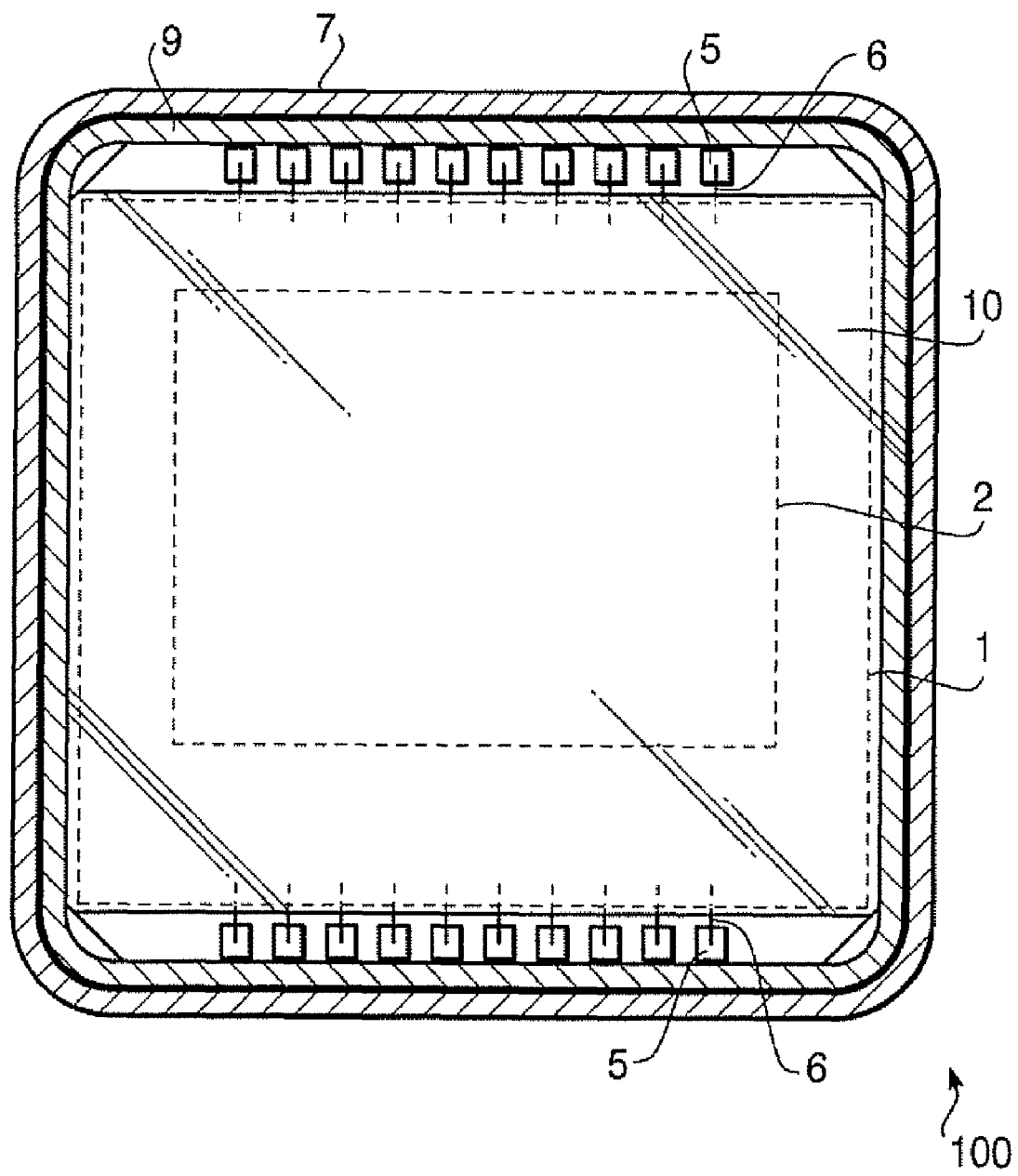
FIG. 2 is a plane view of the image capturing unit taken along a line II-II in FIG. 1 according to the first embodiment of the invention.

FIG. 1 is a cross-sectional side view of an image capturing unit 100 of an electronic endoscope according to a first embodiment of the present invention. FIG. 2 is a plane view of the image capturing unit 100 taken along a line II-II in FIG. 1 according to the first embodiment of the invention. The image capturing unit 100 is provided at a tip of an inserted portion (not shown) of the endoscope and includes a solid-state image capturing element 1, of which a front surface is formed to be an approximate rectangle. Further, an image capturing area 2, which is formed to be an approximate rectangle and substantially smaller than the image capturing element is provided in a central portion of the image capturing element 1.

The image capturing element 1 is supported by an insulated block 3, which is made of an insulated material, such as ceramic. The insulated block 3 is formed to have a recessed portion at a front thereof, so that the image capturing element 1 may be adhesively fixed therein.

On an outer surface of a rear portion of the insulated block 3, a plurality of contact lands 4 that are connected to signal conductors (not shown) are provided. Each of the contact lands 4 is connected to a rear end of one of conductors 5, which are buried in the insulated block 3 and extended in parallel with an axial direction of the inserted portion.

Further, in the image capturing unit 1, a plurality of bonding wires 6, which connect a circuit (not shown) of the image capturing element 1 with the conductors 5, are provided. The bonding wires 6 are arranged along two opposed edges of the image capturing element 1 to extend outwardly so that each of the bonding wires 6 is connected to a front end of each of the conductors 5 that are exposed from two opposed edges (an upper edge and an lower edge in FIG. 1) of a front end of the insulated block 3. Each of the bonding wires 6 is curved toward a front of the image capturing element 1 as the bonding wire 6 extends from the front surface of the image capturing element 1.

The image capturing unit 100 further includes a housing 7, which contains the image capturing element 1 therein. The housing 7 is made of one of metals, and has a shape of a rectangular cylinder that encircles by a front portion of the image capturing unit 100, so that vapor and the like should not enter the image capturing unit 110 during high-pressure and high-temperature steam sterilization.

The image capturing unit 100 includes a rear frame 8, which is made of one of metals, and is arranged on an inner periphery at a rear portion of the housing 7, so that space between the housing 7 and the insulated block 3 is maintained. The rear frame 8 is airtight or hermetically sealed at an entire welding surface A to the housing 7, so that the rear frame 8 is assembled to be integral with the housing 7. Further, the rear frame 8 is airtight or hermetically sealed at an entire seal surface B to the insulated block 3 with a fixing method such as by welding, with an inorganic adhesive agent, for example.

The image capturing unit 100 includes a front frame 9, which is made of one of metals, and is arranged on the inner periphery at a front portion of the housing 7. The front frame 9 is airtight or hermetically sealed at an entire welding surface C to the housing 7, whilst a rear end of the front frame 9 is in contact with the front end of the insulated block 3, so that the housing 7 is stabilized to the insulated block 3 through the front frame 9. Further, a transparent cover glass 10 is provided to seal the front surface of the image capturing element 1 from exterior environment. The cover glass 10 is airtight or hermetically sealed to the front frame 9.

As shown in FIG. 1, a thickness of the front frame 9 (excluding a front-most portion) in a radial direction is formed to be substantially equivalent to a thickness of the housing 7, whilst the front-most portion of the front frame 9 is formed to be thicker in the radial direction. That is, a diameter of the front-most portion of the front frame 9 is configured to be smaller than a diameter of the remaining portion of the front frame 9. With this configuration, the bonding wires 6 and the front end of the conductors 5 can be prevented from coming into contact with the rear end of the front frame 9 when the image capturing unit 100 is assembled, and the cover glass 10 can be attached to a seal surface D of the front-most portion of the front frame 9.

The cover glass 10, which is airtight or hermetically sealed to the seal surface D with an inorganic adhesive agent, is formed to have a shape of an approximate rectangle, which is substantially smaller than the diameter of the front frame 9, and substantially greater than the image capturing area 2 of the image capturing element 1. As shown in FIG. 1, the cover glass 10 is arranged on an outer side of the image capturing area 2, and a length L0 of an edge of the image capturing area 2 is smaller than a length L1 of an edge of the cover glass 10.

The image capturing unit 100 is configured to have the cover glass 10 the cover glass 10 is arranged to be in a position as closest as possible to (but not in contact with) the front surface of the image capturing element 1, so that an entire configuration of the image capturing unit 100 can be downsized. The space between a rear surface of the cover glass 10 and the front surface of the image capturing element 1 is in a range approximately from 0.01 mm to 0.1 mm, for example. Further, the length L1 is configured to be smaller than a length L2, which is a length between contact points of the bonding wires 6 to the front ends of the conductors 5 along the upper edge of the image capturing element 1 and contact points of the bonding wires 6 to the front ends of the conductors 5 along the lower edge of the image capturing element 1.

It should be noted that the cover glass 10 is formed to have bonding wire preventing portions 11 in vicinity to each of an upper rear and a lower rear edges thereof, so that the extending bonding wires 6 may not be interfered with the upper and lower edges of the cover glass 10.

Figure 3:
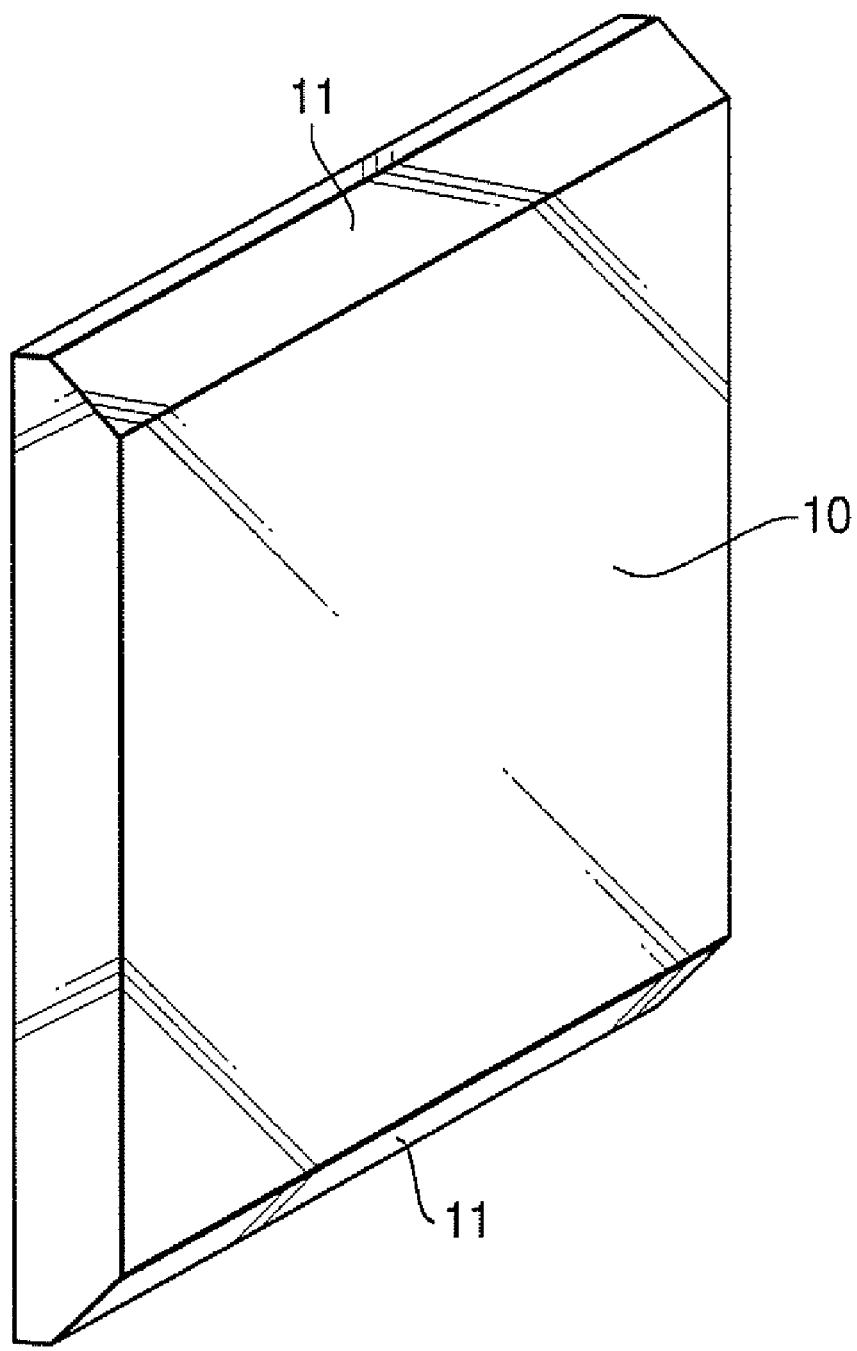
FIG. 3 is a perspective view of a cover glass of the image capturing unit according to the first embodiment of the invention.
Figure 4:
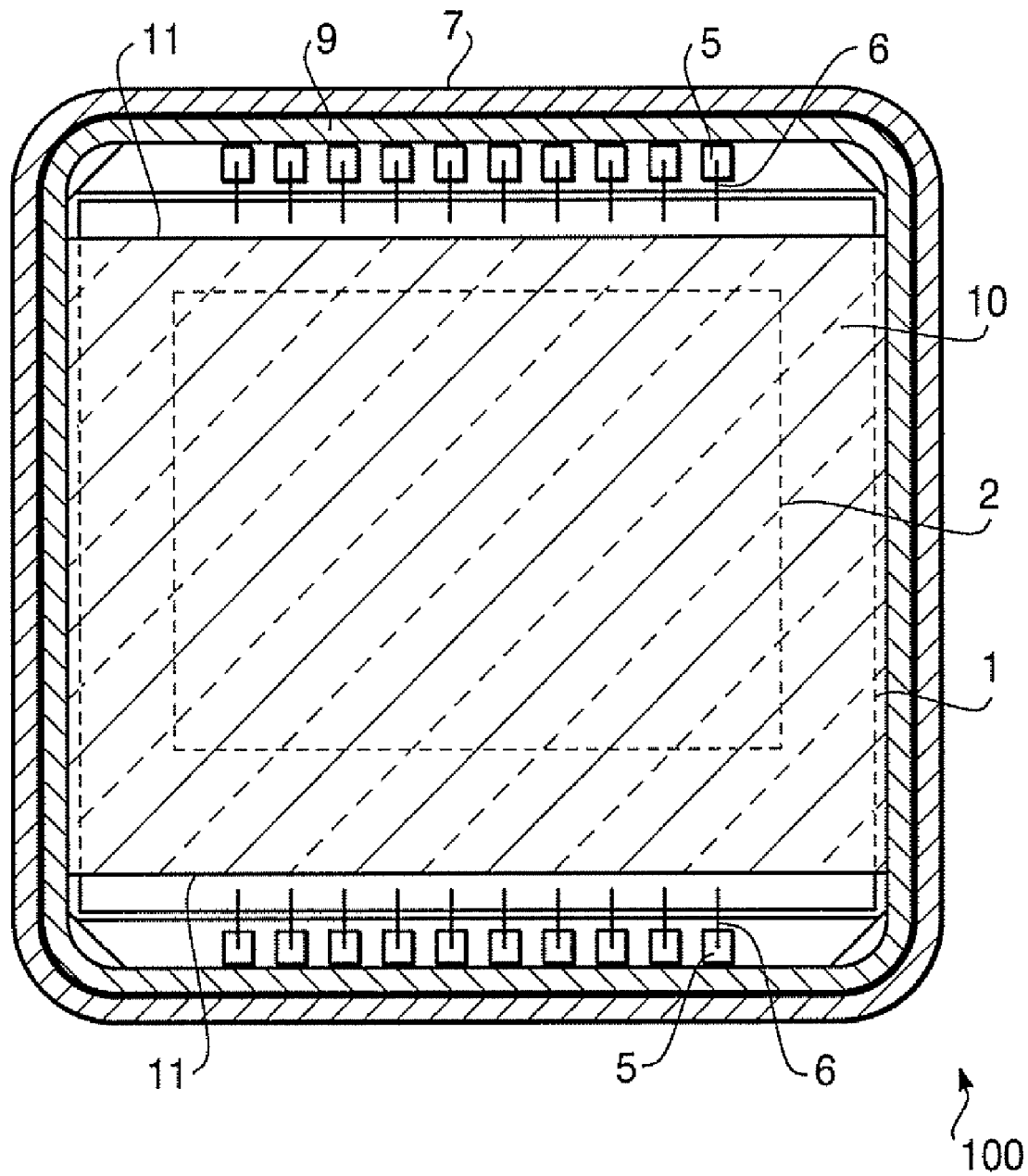
FIG. 4 is a plane view of the image capturing unit taken along a line IV-IV in FIG. 1 according to the first embodiment of the invention.

FIG. 3 is a perspective view of the cover glass 10 of the image capturing unit 100 according to the first embodiment of the invention. FIG. 4 is a plane view of the image capturing unit 100 taken along a line IV-IV in FIG. 1 according to the first embodiment of the invention. As shown in FIG. 3, the bonding wires preventing portions 11 in the present embodiment are formed by beveling the upper rear and the lower rear edges of the cover glass 10 at an angle, for example, at approximately 45 degrees. With this structure the cover glass 10 can be prevented from being in contact with the bonding wires 6, as shown in FIGS. 1 and 4.

With the above configuration, space required in the image capturing unit 100 for the cover glass 10 can be downsized, so that the entire image capturing unit 100 can be configured to be smaller As a result, an endoscope having a tip portion with a diameter being considerably small may be achieved. Further, functionalities of an objective optical system of the endoscope, such as a zooming function, may be improved. Furthermore, the endoscope may become capable of operating in fine movements inside live bodies, so that an aiming functionality to observe an affected region of the live bodies may be improved.

Although examples of carving out the invention have been described, those skilled in the art will appreciate that there are numerous variations and permutations of the image capturing unit and the endoscope that fall within the spirit and scope of the invention as set forth in the appended claims. It is to be understood that the subject matter defined in the appended claims is not necessarily limited to the specific features or act described above. Rather, the specific features and acts described above are disclosed as example forms of implementing the claims.

Figure 5:
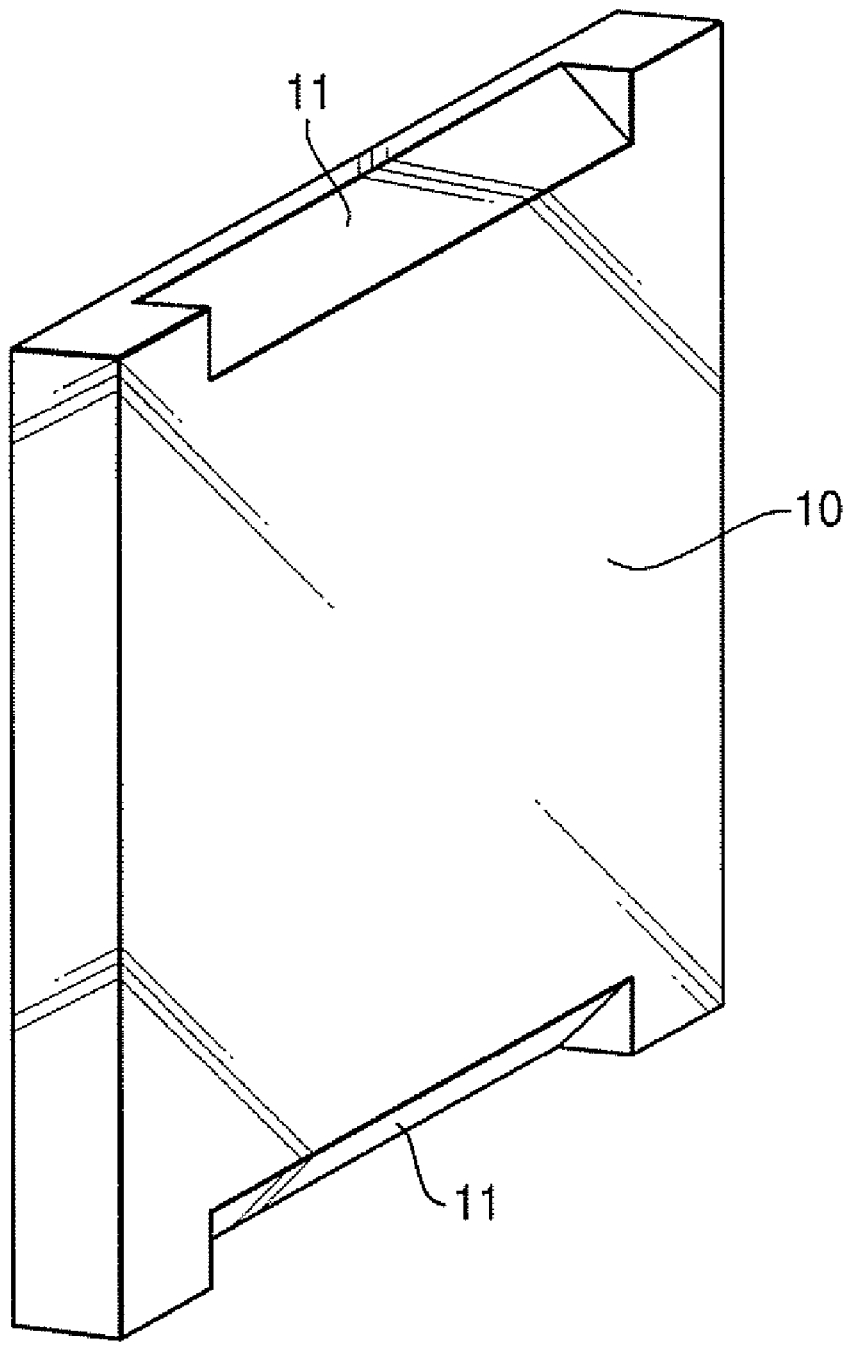
FIG. 5 is a perspective view of a variation of the cover glass of the image capturing unit according to the embodiment of the invention.

FIG. 5 is a perspective view of a variation of the cover glass 10 of the image capturing unit 100 according to an embodiment of the invention. The bonding wire preventing portions 11 may be formed by merely cutting off portions that may otherwise become in contact with the bonding wires 6.

Figure 6:
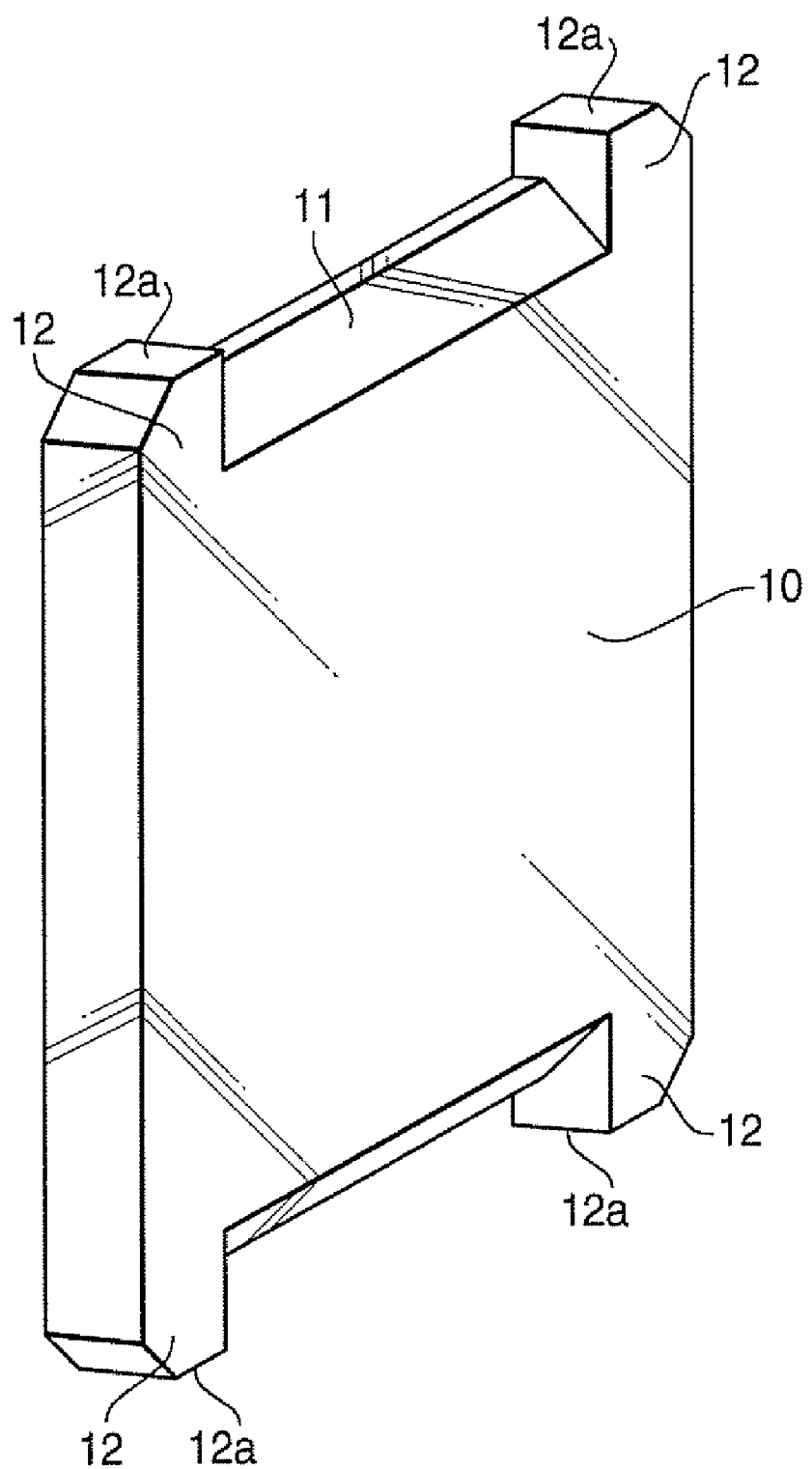
FIG. 6 is a perspective view of another variation of the cover glass of the image capturing unit according to the embodiment of the invention.

FIG. 6 is a perspective view of another variation of the cover glass 10 of the image capturing unit 100 according to an embodiment of the invention. The cover glass 10 is formed to have positioning portions 12, whilst the bonding wire preventing portions 11 are prevented from being in contact with the bonding wires 6. The positioning portions 12 have positioning surfaces 12, which are adapted to be in contact with an inner surface of the front frame 9, so that the cover glass 10 can be easily located in a correct position with respect to the front frame 9. It should be noted that in this configuration the length L1 of the cover glass 10 may be greater than the length L2, whilst the bonding wires 6 are still prevented from being in contact with the cover glass 10.

The present disclosure relates to the subject matter contained in Japanese Patent Application No. P2005-193226, filed on Jul. 1, 2005, which is expressly incorporated herein by reference in its entirety.

What is claimed is:

1. An image capturing unit for an electronic endoscope, comprising:

a solid-state image capturing element with an image capturing area, which is adapted to capture an image of an object;

at least one bonding wire, which is extended curvedly and outwardly from at least one edge portion of a surface of the solid-state image capturing element to at least one conductor, the at least one conductor conducting electricity to the solid-state image capturing element via the at least one bonding wire; and a transparent cover plate, which is fixed to a frame so that the transparent cover plate is arranged in front of the solid-state image capturing element, and is adapted to seal the solid-state image capturing element from an external environment, wherein the transparent cover plate is formed to have at least one bonding wire preventing portion, which is adapted to prevent the at least one bonding wire from being in contact with the transparent cover plate, so that the at least one bonding wire is prevented from being interfered by the transparent cover plate when the transparent cover plate is arranged in a position closer to the image capturing element than a position wherein a cover plate without the bonding wire preventing portion is required to be placed, wherein an edge portion on a front surface of the transparent cover plate is hermetically sealed to the frame, and wherein the at least one bonding wire preventing portion is formed by beveling a rear edge of the cover plate.

2. The image capturing unit according to claim 1, wherein a length between outermost edges of the transparent cover plate is configured to be greater than a length between outermost edges of the image capturing area of the image capturing element and to be smaller than a length between a contact point of the at least one bonding wire to the conductor along a first edge of the image capturing element and a contact point of the at least one bonding wire to the conductor along a second edge of the image capturing element.

3. An image capturing unit for an electronic endoscope, comprising:

an image capturing element that captures an image of an object;

a bonding wire that extends outwardly from an edge portion of a surface of the image capturing element to carry an electrical signal; and a transparent cover plate hermetically sealed to a frame arranged in front of the image capturing element to environmentally seal the image capturing element, the transparent cover plate including a bonding wire preventing portion that prevents the bonding wire from contacting the transparent cover plate, the bonding wire preventing portion being formed by beveling a rear edge of the transparent cover plate.

* * * * *